United States Patent [19]

Ray et al.

[11] Patent Number: 4,784,737

[45] Date of Patent: Nov. 15, 1988

[54] ELECTROMICROINJECTION OF PARTICLES INTO LIVING CELLS

[75] Inventors: F. Andrew Ray; L. Scott Cram, both of Los Alamos; William R. Galey, Albuquerque, all of N. Mex.

[73] Assignee: The United States Department of Energy, Washington, D.C.

[21] Appl. No.: 853,823

[22] Filed: Apr. 18, 1986

[51] Int. Cl.$^4$ .................. B01D 57/02; A61N 1/30; A61B 17/36; C12N 15/00

[52] U.S. Cl. ...................... 204/180.1; 204/299 R; 604/21; 128/303.18; 128/784; 128/786; 435/296; 435/172.1; 435/172.2; 435/172.3

[58] Field of Search ............... 604/20, 21; 128/303.18, 128/784, 786; 435/296, 172.1, 172.2, 172.3; 204/180.1, 299 R, 403, 164, 165

[56] References Cited

PUBLICATIONS

Elaine G. Diacumakos et al., "A Microsurgical Methology for Human Cells in Vitro: Evolution and Applications," 65 Proc. Nat. Acad. Sci., (No. 4), 911 (1970).
Elaine G. Diacumakos, "Methods for Micromanipulation of Human Somatic Cells in Culture,", in *Methods in Cell Biology*, (Academic Press, Inc., New York, 1973), vol. VII, Chap. 17, p. 287.
Munehiko Ocho et al., "Microinjection of Nucleic Acids into Cultured Mammalian Cells by Electrophoresis", 35 Acta. Med. Okayama, (5), 381 (1981).
F. Andrew Ray, "The Introduction of Morphologically Intact Human Chromosomes Into Chinese Hamster Mitotic Cells by Electromicroinjection", thesis submitted in partial fulfillment of requirements for the degree of Master of Science in Medical Sciences.

*Primary Examiner*—John F. Niebling
*Assistant Examiner*—Ben C. Hsing
*Attorney, Agent, or Firm*—Samuel M. Freund; Paul D. Gaetjens; Judson R. Hightower

[57] ABSTRACT

Method and apparatus for introducing particles into living cells. Fluorescently-stained human chromosomes are introduced into cultured, mitotic Chinese hamster cells using electromicroinjection. The recipient cells frequently survived the physiological perturbation imposed by a successful chromosome injection. Successfully injected recipient cells maintained viability as evidenced by their ability to be expanded.

The technique relies on the surface charge of fluorescently stained chromosomes and their ability to be attracted and repelled to and from the tip of a micropipette. The apparatus includes a micropipette having a tip suitable for piercing the membrane of a target cell and an electrode inserted into the lumen thereof. The target cells and suspended particles are located in an electrically conducted solution, and the lumen of the micropipette is filled with an electrically conducting solution which contacts the electrode located therein. A second electrode is also located in the conducting solution containing the target cells and particles. Voltages applied to the electrode within the micropipette attract the particles to the region of the tip thereof. The particles adhere to the surface of the micropipette with sufficient force that insertion of the micropipette tip and attached particle through the membrane of a target cell will not dislodge the particle. By applying a voltage having the opposite polarity of the attraction voltage, the particles are expelled from the micropipette to which is then withdrawn from the cell body.

11 Claims, 3 Drawing Sheets

ELECTROMICROINJECTION OF PARTICLES INTO LIVING CELLS

This invention is the result of a contract with the Department of Energy (Contract No. W-7405-ENG-36).

BACKGROUND OF THE INVENTION

The present invention relates generally to microinjection and more particularly to an electromicroinjection of macroscopic particles such as whole chromosomes into living cells.

Relatively pure chromosomes of a single type can be obtained by flow sorting. An extra copy of certain chromosomes has been shown to have biological effects due to increased gene dosage. Important questions involving gene dosage effects relative to tumorigenicity could be addressed if specific intact chromosomes could be introduced into various mammalian somatic cell types. There are several methods which have been used to alter the chromosome number of mammalian cells and study gene dosage. Fusion of two cell types, for example, relies on the gradual loss of chromosomes from the resulting hybrid cells but is often difficult to clearly interpret due to the heterogeneous nature of these hybrids. Whole chromosomes have been transferred by microcell fusion. However, many microcell hybrids have to be screened because the microcells rarely contain single chromosomes.

The most direct method for transfer of chromosomes is by microinjection. Previously reported microinjection techniques suffer from limitations in cell recovery. See, e.g., "A Microsurgical Methodology for Human Cells in Vitro: Evolution and Applications," by H. G. Diacumakos, S. Holland, and P. Pecora, Proc. Nat. Acad. Sci. 65, 911 (1970), and "Methods for Micromanipulation of Human Somatic Cells in Culture," by E. G. Diacumakos, reprinted from: Methods in Cell Biology, Vol VII, Ch. 15 (Academic Press, Inc., New York, 1973), p. 287 ff. for a description of developed procedures for manipulating chromosomes within living cells. The disclosure of the latter reference is hereby incorporated by reference herein. The former publication reports the only instance where a single chromosome was transferred from one human embryonic lung mitotic cell to another. The chromosome was dissected free from the donor cell, aspirated into a micropipette and injected into a second mitotic cell. Although the recipient cell survived the procedure and completed mitosis, it did not divide again. It was not possible to determine whether the cell was irreparably damaged by the operation, was affected by a gene on the introduced chromosome, or was incapable of growth as a single isolated cell. Clearly, a less invasive procedure would prove most valuable.

In "Microinjection of Nucleic Acids into Cultured Mammalian Cells by Electrophoresis," by M. Ocho. S. Nakai, K. Tasaka, S. Watanabe, and T. Oda, Acta Med. Okayama 35, 381 (1981), the authors describe an electrophoretic apparatus for microinjection of DNA from a conducting solution in which the DNA is dissolved into living cells. An electrode is inserted into a micropipette filled with the solution containing the molecules to be injected into the cells and placed in electrical contact with a high input-impedance preamplifier. A second electrode is placed in a conducting solution containing the cells. When the micropipette is placed in this solution an electric circuit is completed. From the impedances and the currents disclosed, one may calculate that the authors applied approximately 100 V to the microelectrode in the form of 25 ms duration, 10 Hz square waves for 5 s. No mention is made therein of the microinjection of particles not dissolved in the solution, and more particularly, no mention is made of any requirement to reverse the polarity of the applied voltage to complete the microinjection process. Moreover, the micropipette of Ocho et al. is filled in the normal manner from the end thereof away from the tip. That is, there is no teaching of attraction of the material to be injected into the cell to the tip of the micropipette by the application of a voltage thereto.

"The Introduction of Morphologically Intact Human Chromosomes into Chinese Hamster Mitotic Cells by Electromicroinjection," by F. A. Ray, W. R. Galey, J. H. Jett, and L. S. Cram, submitted for publication to Experimental Cell Research contains a more detailed account of the use of the present invention to introduce morphologically intact human chromosomes into Chinese hamster mitotic cells by the apparatus and method hereof, as does "The Introduction of Morphologically Intact Human Chromosomes into Chinese Hamster Mitotic Cells by Electromicroinjection," by F. Andrew Ray, thesis submitted in partial fulfillment of the requirements for the degree of Master of Science in Medical Sciences, The University of New Mexico, April 1985, the disclosure of the latter document hereby being incorporated by reference herein.

SUMMARY OF THE INVENTION

Accordingly. it is an object of the present invention to provide an apparatus and method for the introduction of particles not dissolved in solution into living cells.

Another object of the invention is to provide an apparatus and method for introducing particles in fluid suspension into living cells without causing significant cell disruption.

Yet another object of the present invention is to provide an apparatus and method for introducing morphologically intact human chromosomes into living cells without causing significant cell disruption.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus of this invention includes an injection micropipette having an exit orifice size suitable for piercing the membrane of a target recipient cell, an electrically conducting medium located within the lumen thereof and filling the exit orifice of the micropipette, first electrode means located within the lumen of the micropipette as close to the exit orifice as the size of the lumen permits and at least contacting the conducting medium located therein, second electrode means located within the conducting solution which contains the recipient target cells, and means for impressing a first and subsequently a second voltage having the opposite polarity to the first voltage between the first electrode means and the second electrode means. The first voltage may be continuously applied to the electrodes or pulsed and is intended to attract a suspended particle in the conducting solution to the tip of the micropipette and hold it there during insertion of the micropipette and the attached particle through the membrane of a target recipient cell and into the cell proper. The second voltage which is applied subsequently to the first voltage is used to release the particle from the tip of the micropipette and also may be continuously applied or pulsed. Voltages and duration of application thereof are chosen in such a manner so as to induce the least disruption in the target cell during the insertion of the particle and subsequent release thereof.

In a further aspect of the present invention, in accordance with its objects and purposes, the apparatus hereof also includes a micropipette having a conducting surface in the vicinity of the exit orifice thereof, and on its outside surface. This conducting surface provides the first electrode means described in the embodiment previously set forth. The remainder of the elements remain essentially the same.

In yet another aspect of the present invention. in accordance with its objects and purposes, the apparatus hereof also includes a solid conducting microneedle for piercing the cell membrane. The remainder of the apparatus is similar to what is described hereinabove. The solid microneedle might be fabricated from an insulating material and have a conducting material on its outer surface in the vicinity of the needle tip.

In another aspect of our invention. in accordance with its objects and purposes, the method hereof includes attracting at least one particle to the tip of either a micropipette or a microneedle by applying a first voltage between the tip and a conducting aqueous solution containing the particles to be injected, inserting the tip into a target recipient cell present in either the conducting aqueous solution containing the particle, or another aqueous solution, and releasing the at least one particle from the tip by applying a second voltage between the tip and the conducting aqueous solution containing the target cell, the second voltage having a polarity opposite to that of the first voltage. The first and second voltages may be continuously applied or may be pulsed, and the magnitudes and duration of application thereof are chosen so as to induce the least disruption of the target recipient cell during the process of insertion of the particle.

Benefits and advantages of the present apparatus and method include a significantly improved likelihood that the target recipient cell will survive the insertion and release process. Previous microinjection processes which transfer the particle by simply injecting the particle into the cell using hydraulic pressure; that is, by pressurizing the micropipette containing the suspended particle and forcing the particle and a significant amount of the suspending liquid into the cell, have been largely unsuccessful due to the disturbance of the cell during this process. Moreover, hydraulic pressure techniques are not very reliable in placing the chromosomes within the cell membrane since the chromosomes tend to remain adhered to the sides of the micropipette after the maximum quantity of carrier fluid is released to the cell.

BRIEF DESCRIPTION OF THE DRAWINGS

The accompanying drawings, which are incorporated in and form a part of the specification, illustrate one embodiment of the present invention and, together with the description, serve to explain the principles of the invention. In the drawings.

DETAILED DESCRIPTION OF THE INVENTION

Briefly, the present invention includes a method and apparatus for insertion of particles in suspension in a conducting aqueous solution into living cells without seriously disrupting the target recipient cell. A voltage is applied between a micropi-pette or a microneedle having a tip having suitable dimensions to permit insertion thereof through a cell membrane and into the cell body and a second electrode located in the conducting aqueous solution containing the particles. This will attract at least one particle thereto if the tip is moved sufficiently close to the particle. It has been found that the particle adheres to the surface of the tip during the insertion process without the requirement that the voltage be applied continuously. However, it is contemplated that there may be some situations involving certain particles and certain materials of construction for the tip where it will be necessary to maintain the voltage during the insertion process. After insertion, a second voltage is applied to the tip for the purpose of repelling the particle therefrom, this second voltage having a polarity opposite to that of the first voltage. Voltage magnitudes and durations of application are chosen to achieve the intended particle introduction while providing the minimum disruption to the target cell. When the micropipette is employed according to the teachings of our invention, small amounts of fluids of interest may also be placed into the cell body.

Figure 1:
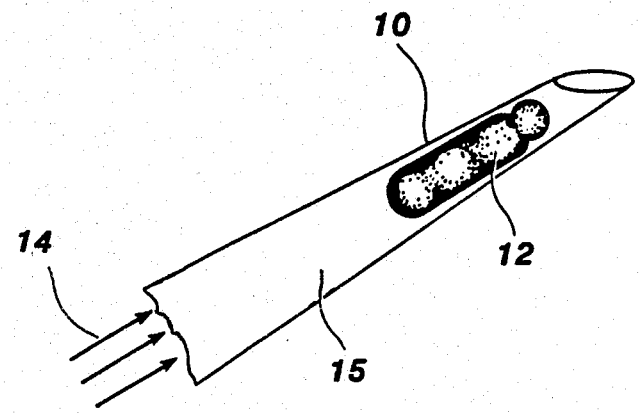
FIG. 1 shows a schematic representation of a micropipette tip utilized in prior microinjection prcedures. Therein, the particle to be injected and suspended in a chosen solution is drawn up into the micropipette along with this solution, and expelled into the recipient target cell by hydraulic pressure applied to the micropipette after insertion of the micropipette tip into the cell body.

Reference will now be made in detail to the present preferred embodiment of the invention, an example of which is illustrated in the accompanying drawings. Turning to FIG. 1, the prior art for microinjection is summarized by the schematic representation of a micropipette tip 10 having sufficient lumen size to accept a particle 12 to be injected into a cell. The force for the expulsion of this particle into the cell after the insertion of the micropipette tip through the cell membrane is derived from pressure 14 applied to the supporting fluid 15. As mentioned hereinabove, this process has not proven to have general effectiveness. The introduction of a significant amount of fluid into the cell during the expulsion process has a disruptive effect on the cell. Many do not recover. Others are materially altered. Moreover, it is often the situation that the particle cannot be expelled from the micropipette by the flow of the supporting fluid due to electrostatic attraction between the particle and the micropipette.

Figure 2:
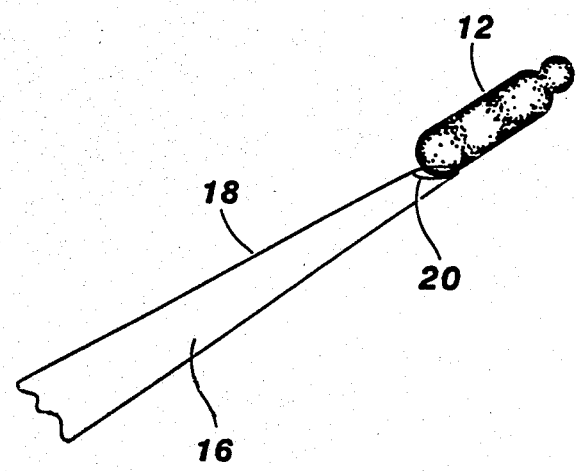
FIG. 2 shows a schematic representation of a micropipette tip according to the teachings of the present invention. A much smaller tip may be utilized since the particle to be inserted is attracted to the tip thereof and held there during the insertion process.

FIG. 2 shows a schematic representation of a micropipette tip 18 according to the teachings of the present invention. The chromosome or other particle 12 is attracted to the outside surface of the micropipette tip and does not have to be located within the lumen of the micropipette prior to the insertion of the micropipette tip through a cell membrane. This permits the orifice size 20 of the micropipette tip to be made smaller (in the range of between 0.1 and 0.5 $\mu$m) than if the particle had to pass therethrough, thereby minimizing damage to the target recipient cells. In the case where small quantities of fluids are to be injected into the cell along with the particle, a micropipette bearing such fluids 16 is the instrument of choice for the microinjection process. However, if no fluids are required, a microneedle would perform the required task.

Figure 3:
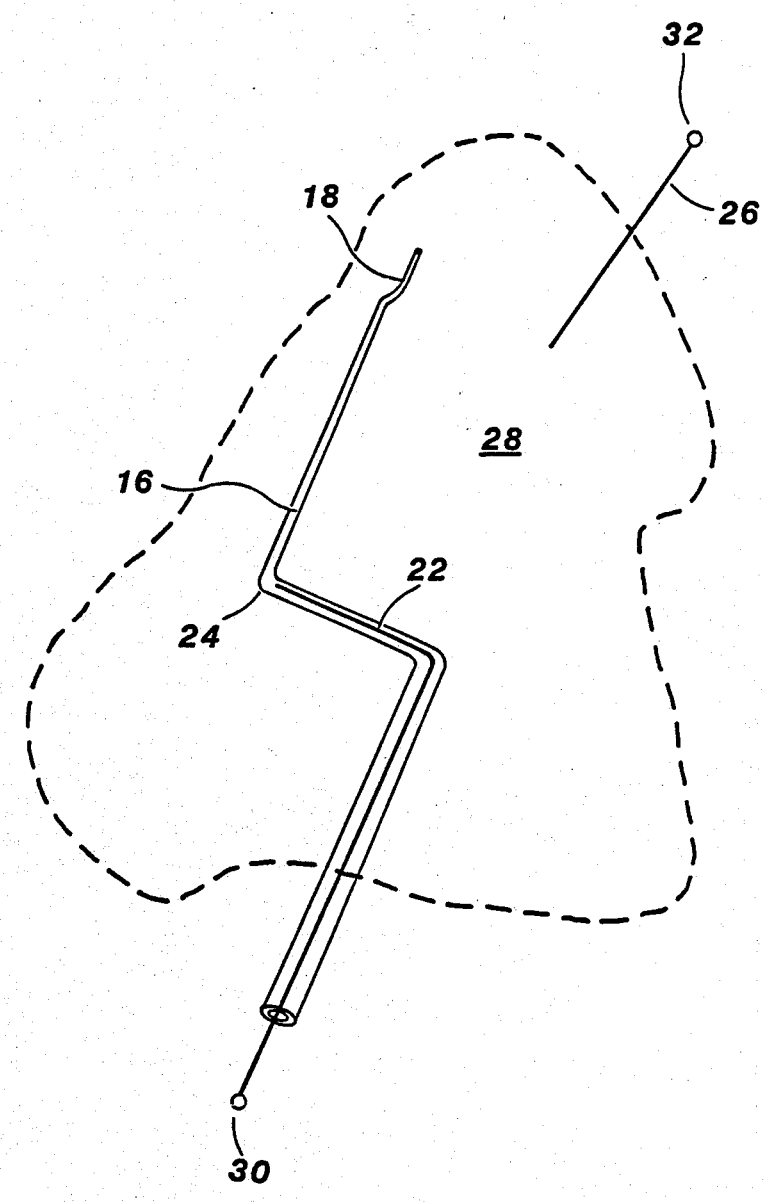
FIG. 3 shows a schematic representation of a greater portion of the micropipette according to the teachings of our invention, the tip of which is shown in FIG. 2 hereof. Shown is the first electrode which is inserted as far into the micropipette as the lumen thereof permits.

FIG. 3 shows a schematic representation of a greater portion of the micropipette of the present invention 18. First electrode 22 is inserted into the lumen of the micropipette to a location within the vicinity of the second right angle bend thereof 24. A second electrode 26 is placed into an electrically conducting medium 28 which contains the particles to be injected into the cells and the recipient target cells. It is also contemplated that the particles to be injected and the target cells may not be in the same conducting solution. In this situation, the micropipette or microneedle would be moved from the solution containing the particles to the one containing the target cells after attachment of a particle or particles to the tip thereof. The second electrode would also be moved in order to provide a complete electrical circuit. The first electrode 22 must at least be in contact with an electrically conducting medium 16 which may have the same composition as the electrically conducting medium 28 containing the particles and the target cells, or may have a different composition for the purpose of introducing additional materials into the cell body other than the particle or particles. If a microneedle is employed, the first electrode would then be the microneedle itself which would be fabricated from electrically conducting materials. Moreover, it is further contemplated that the first electrode might be a region of electrically conducting material on the outer surface of the micropipette or a conducting microneedle in the vicinity of the exit orifice or tip, respectively. In every event, the first electrode is connected 30 to a source of voltage at the end thereof away from the tip or exit orifice to be inserted through the cell membrane. Similarly, the second electrode 26 is connected to the source of voltage at location 32.

Figure 4:
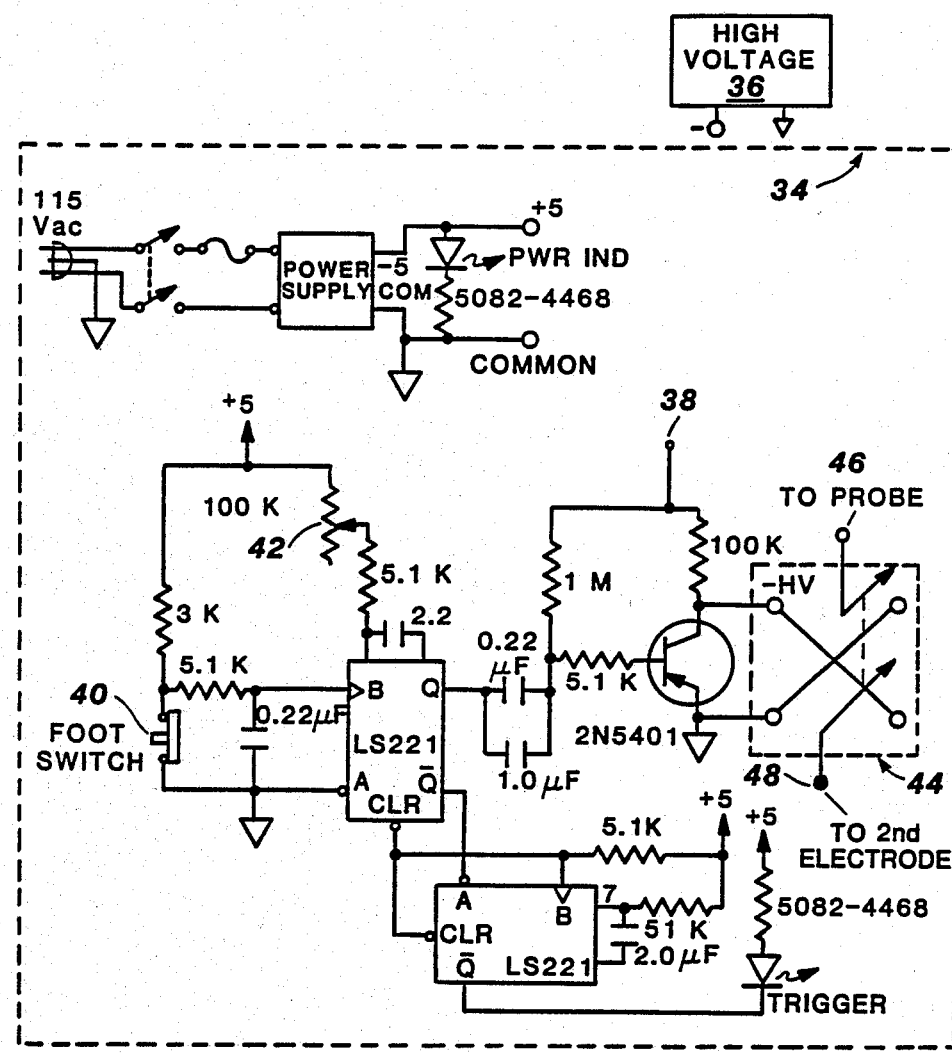
FIG. 4 is a schematic representation of the electric circuit used to supply pulsed first and second voltages to the electrode within the micropipette shown in FIG. 3 hereof. Clearly many circuits are possible to achieve the same result.

FIG. 4 shows a schematic representation of the pulser 34 utilized to provide the pulsed voltages to the micropipette or microneedle. High voltage source 36 generates the requisite negative voltage to terminal 38 of the pulser. A one-shot integrated circuit pulses once and then must be retriggered. The firing of the pulser is controlled by means of foot switch 40 in order to maintain freedom of the hands. A potentiometer 42 permitted the pulse width of the voltage pulse to be varied from 12 to 255 ms, but clearly a wider range of pulse widths is usable. For example, pulse durations in the range from 1 ms to dc are believed by the inventors to be useful. The microprobe output was directed to 3-way switch 44 to enable the polarity of the voltage pulse to be reversed in order that either electrode might be made positive or negative relative to the other. The third position of this switch was off. Terminal 46 thereof was connected to the first electrode at connection point 30 thereof, while terminal 48 of the 3-way switch was connected to the second electrode located in the conducting solution at connection point 32 thereof (see also FIG. 3 hereof).

Having generally specified the invention, the following specific example is given as a further illustration thereof.

EXAMPLE

As an example of the use of the apparatus and method of the present invention for introducing particles into living cells, morphologically intact human chromosomes were introduced into Chinese hamster mitotic cells. The microinjection procedure developed by Diacumakos, supra, was chosen since it allows the visualization of the target cells at high magnification. Moreover, the injection chamber can be maintained sterilely and the injected cell cloned immediately after injection without biochemical selection steps. In attempts to repeat the experiments described therein, it was found that the chromosomes adhered inside the orifice of the micropipettes and could not be dislodged. This result may be a surface charge phenomenon. Therefore, the present apparatus and method was employed. A silver electrode was placed inside the micropipette and a second electrode placed in the injection chamber to be described hereinbelow. It was found that single chromosomes floating within the chamber could be attracted to the tip of the micropipette from any direction by the application of a small electrical pulse. A second pulse, having opposite polarity, was applied after the micropipette tip and the attached chromosome were inserted into the cell body through the cell membrane in order to release the chromosome. Chinese hamster tetraploid cells were employed as the recipient cells in the initial tests of the present invention because of their large size and secure substrate attachment. Large cells were preferred during the development of this technique to increase the survival frequency of the recipient cells since fully condensed metaphase chromosomes are relatively large particles when compared to a diploid cell. Normal human fibroblast cell strains were used as a source of chromosomes in order to facilitate the assay of recipient cells for an additional chromosome if the cells survived the injection procedure, since human chromosomes can be readily identified in a Chinese hamster cell by G-11 staining. Chromosome isolation procedures were developed to leave the chromosome morphologically intact and yet not expose them to nonphysiological agents which have frequently been used to prepare chromosome suspensions. Prior to injection the chromosomes were resuspended in a solution designed to closely approximate the internal physiological milieu of the recipient cells. Mitotic cells were chosen as recipient cells in order to minimize recipient cell damage by penetrating only one membrane, in order to avoid premature chromosome condensation which is generally caused when a mitotic cell is fused to an interphase cell, and in order to place the chromosome in the same stage of the cell cycle from which it came.

Accordingly, tetraploid clones of a Chinese hamster cell line (WCHE 5) were used for recipient cells, and a normal human diploid strain (HSF 7) of foreskin derived fibroblast-like cells was used for chromosome donors. All cells were maintained in αMEM with 10% fetal calf serum. A chromosome isolation procedure used to isolate chromosomes for flow cytometric analysis and sorting was adapted to maintain the chromosome suspensions as physiologically compatible with recipient cells as possible and yet preserve the resolution necessary for sorting by flow cytometry. Cells were blocked overnight (12-16 h) with colcemid (0.1 µg/ml, mitotics were dislodged by mitotic shake-off, concentrated by centrifugation at 200×G for 10 min and swollen for one hour in a solution comprising: 50 mM KCl, 10 mM MgSO$_4$ and 1 µM Hoechst 33342 (kept in darkness). RNAase, detergents, and dithiothreitol were omitted, hence the longer swelling time. After swelling, the cells were forcefully syringed 3-4 times through a 22 gauge needle on a 5.0 ml syringe. The chromosomes were prepared sterilely. If the chromosomes were to be used for flow cytometry and sorting, the Hoechst (HO) concentration was increased to 10.0 µM. If they were to be used directly for microinjection, the chromosomes were centrifuged 30 minutes at 100×G (4° C.). The chromosomes were then resuspended in a physiological injection buffer (PIB) consisting of 111.5 mM KCl, 20.0 mM NaCl, 3 mM MgCl$_2$, 1.5 mM KH$_2$PO$_4$ and 1.5 mM Na$_2$HPO$_4$ and having a pH of 6.8. This step was designed to remove unbound or loosely bound stain.

Chromosome morphology was well preserved after preparation of chromosome suspensions. Donor chromosomes were selected on the basis of visual examination using phase contrast microscopy. Only well-preserved chromosomes with clearly defined centromeric constrictions were selected for injection. The resolution of the flow karyotype provides additional evidence as to the intactness of the donor chromosomes.

The general microinjection protocol was similar to that described by Diacumakos, supra. Cells were grown on glass cover slips. The cover slips with attached cells were inverted over a sealed chamber containing sterile media. A 1 mm diameter circle was then scribed around recipient cells. Selective detachment left individual recipient cells alone within the scribed circle. Recipient cells were cloned by physical transfer of the glass circle upon which it was growing. The major modification to the Diacumakos procedure was the use of electrostatic attraction and repulsion of chromosomes in place of pressure injection.

The current generated was measured at various dc voltages. For example, at 400 V, a 0.1-0.4 µm micropipette orifice allowed a 4.0 µA current. However, when the microprobe pulse was employed, the applied voltage was kept below about 100 V. The output polarity of the microprobe pulser can be reversed so that either electrode is positive or negative as desired. The output thereof was connected to silver electrodes (0.005 in. diameter). One electrode was run directly down the injection micropipette to where the lumen narrowed, and the other was placed in the media within the injection chamber. The electrodes were abraded with a fine emery paper and washed with 70% ethanol prior to each use.

Injection chambers were constructed in a similar manner to those described by Diacumakos, supra, but with small modifications. Parallel 1 in. × ¼ in. supporting struts were used which left only two sides to be sealed with silicon oil. The chambers were placed in an incubator at 37° C. for a period of time, and then placed on the stage of a microscope. The micropipette was subsequently aligned inside the chamber. A test injection was performed to insure that the micropipette tip was unclogged. A positive 100 V pulse was applied for 132 msec within an interphase cell. If the system was working, a small change in the refractive index was observed due to the small amount of aqueous solution injected.

At this point, 0.1 ml of sterile chromosomes was added to the injection chamber. After electrostatic attraction of a chromosome from suspension, the chromosome was inserted through the plasma membrane. A second electric pulse of opposite polarity was then applied to dislodge the chromosome. Verification of chromosome injection was achieved by observing the fluorescent chromosome within the recipient cell. The fluorescent dyes used were specific for DNA and therefore proved that the object on the micropipette tip and within a mitotic cell was a chromosome. It is not known what effects DNA-specific dyes have on recipient cells. HO and propidium iodide (PI) have both been reported to be mutagenic. It is contemplated by the present inventors that under certain circumstances a continuously applied voltage may be required instead of the pulsed voltages described hereinabove.

Chromosome transfer was nearly 50% successful after technical proficiency had increased. A large percentage of the cells receiving a chromosome in these attempts (70%) survived and completed mitosis. Twenty percent of the cells continued to divide and were expanded to millions of cells. One of these two cells received a PI-stained stained chromosome and the other received an HO-stained chromosome. G-11 staining was applied to metaphase spreads of the expanded cell populations. In neither case, when the recipient cell was expanded to millions of cells, was a human chromosome detected in the Chinese hamster background.

PI-stained chromosomes were usually attracted to a positive polarity (73%). Occasionally, chromosomes were attracted to a negatively charged pipette but were firmly seated over the orifice by a positive pulse. The surface charge of the HO-stained chromosomes was more variable than that of the PI-stained chromosome. In 66% of the chromosomes investigated, a negative charge was used to successfully capture an HO-stained chromosome. Twenty-five percent of attempts succeeded in capturing the stained chromosome with a positive pulse similar to the PI-stained chromosomes. Additionally, when the chromosomes were stained with HO, they were more loosely attached to the tip of the micropipette. The most frequent cause for failure of an injection attempt was for the chromosome to slide down the pipette tip or stick to the plasma membrane during penetration thereof by the micropipette. Conversely, PI-stained chromosomes were more firmly attached and the most frequent cause of failure for a chromosome transfer was to have the chromosome remain attached to the tip after reversing the electrical pulse. Chromosomes were found to remain morphologically intact and appeared very flexible during the injection process.

The foregoing description of a preferred embodiment of the invention has been presented for purposes of illustration and description. It is not intended to be exhaustive or to limit the invention to the precise form disclosed. and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. An apparatus for introducing individual particles suspended in an electrically conducting aqueous solution into recipient biological cells. the apparatus comprising in combination:

an injection micropipette having an exit orifice size for piercing the membrane of a target recipient cell and an entrance orifice;

an electrically conducting medium located within the lumen of said injection micropipette in contact with the exit orifice thereof;

first electrode means located within the lumen of said injection micropipette, said first electrode means having a first end positioned within said electrically conducting medium contained in the lumen of said injection micropipette, and a second end which emerges from the entrance orifice thereof;

second electrode means located in the electrically conducting aqueous solution containing the recipient biological cells; and means for applying a first voltage and a subsequent second voltage between the second end of said first electrode means and said second electrode means both when the exit orifice of said injection micropipette is located in the conducting aqueous solution and when the exit orifice of said injection micropipette is located within the body of a recipient cell located in the conducting aqueous solution, the first voltage having a chosen magnitude and polarity for electrostatically attracting at least one particle to the region of the exit orifice of said injection micropipette, and for holding the particle in this location during the process of piercing the membrane of a cell with the exit orifice of said injection micropipette and insertion of the particle into the recipient cell body. and the second voltage having a polarity opposite to that of the first voltage and a chosen magnitude for electrostatically repelling the particle away from the injection micropipette.

2. The apparatus as described in claim 1, wherein the first voltage and the second voltage are pulsed voltages having a duration between about 1 and 300 ms.

3. The apparatus as described in claim 1, wherein the first voltage is a dc voltage and the second voltage is a pulsed voltage.

4. The apparatus as described in claims 1, 2 or 3, wherein the chosen magnitude of the first voltage and the chosen magnitude of the second voltage are between about 5 and 150 V.

5. The apparatus as described in claim 4, wherein said conducting medium comprises material to be injected into the target recipient cell.

6. A method for introducing individual particles suspended in an electrically conducting aqueous solution into recipient biological cells. the method comprising the steps of:

attracting at least one of the individual particles to the tip of a micropipette for piercing the membrane of a target recipient cell and located in the conducting aqueous solution containing the target recipient cells by applying a first voltage between the tip of the micropipette and the conducting aqueous solution:

inserting the micropipette tip into a target recipient cell, the at least one particle remaining attached thereto during said insertion step; and releasing the at least one particle from the tip of the micropipette by applying a second voltage between the tip of the micropipette and the conducting aqueous solution. the second voltage having a polarity opposite to that of the first voltage.

7. The method as described in claim 6, wherein the first applied voltage is maintained during said insertion step.

8. The method as described in claim 6. wherein the first applied voltage and the second applied voltage are pulsed voltages.

9. An apparatus for introducing individual particles suspended in an electrically conducting aqueous solution into recipient biological cells, the apparatus comprising in combination:

an injection micropipette having an exit orifice size for piercing the membrane of a target recipient cell, the outside surface of said injection micropipette having a conducting material thereon in the region of the exit orifice;

first electrode means for providing electrical contact with the conducting material at a location away from the exit orifice;

second electrode means located in the electrically conducting aqueous solution containing the recipient biological cells; and means for providing a first voltage and a second voltage between said first electrode means and said second electrode means both when the exit orifice of said injection micropipette is located in the conducting aqueous solution and when the exit orifice of said injection micropipette is located within the body of a recipient cell located in the conducting aqueous solution, the first voltage having a chosen magnitude and polarity for electrostatically attracting at least one particle to the region of the exit orifice of said injection micropipette, and for holding the particle in this location during the process of piercing the membrane of a cell with the exit orifice of said injection micropipette and insertion of the particle into the recipient cell body, and the second voltage having a polarity opposite to that of the first voltage and a chosen magnitude for electrostatically repelling the particle away from the injection micropipette.

10. The apparatus as described in claim 9, wherein said injection micropipette contains material to be injected into the target recipient cell.

11. An apparatus for introducing individual particles suspended in an electrically conducting aqueous solution into recipient biological cells. the apparatus comprising in combination:

a conducting microneedle having a tip size for piercing the membrane of a target recipient cell;

electrode means located in the electrically conducting aqueous solution containing the recipient biological cells; and means for providing a first voltage and a second voltage between the tip of said conducting microneedle and said electrode means both when the tip of said conducting microneedle is located in the conducting aqueous solution and when the tip of said conducting microneedle is located within the body of a recipient cell located in the conducting aqueous solution, the first voltage having a chosen magnitude and polarity for electrostatically attracting at least one particle to the region of the exit orifice of said injection micropipette, and for holding the particle in this location during the process of piercing the membrane of a cell with the tip of said conducting microneedle and insertion of the particle into the recipient cell body, and the second voltage having a polarity opposite to that of the first voltage and a chosen magnitude for electrostatically repelling the particle away from the conducting microneedle.

* * * * *